United States Patent [19]

Kelbaugh et al.

[11] 4,147,797

[45] Apr. 3, 1979

[54] SPIRO-FURANOHYDANTOIN DERIVATIVES

[75] Inventors: Paul R. Kelbaugh, Niantic; Reinhard Sarges, Mystic, both of Conn.

[73] Assignee: Pfizer Inc., New York, N.Y.

[21] Appl. No.: 932,990

[22] Filed: Aug. 11, 1978

[51] Int. Cl.$^2$ .................. A61K 31/415; C07D 491/10
[52] U.S. Cl. .................................. 424/273 R; 548/309
[58] Field of Search ...................... 548/309; 424/273 R

[56] References Cited
U.S. PATENT DOCUMENTS

| | | | |
|---|---|---|---|
| 3,821,383 | 6/1974 | Sestanj | 424/258 |
| 4,117,230 | 9/1978 | Sarges | 548/309 |

FOREIGN PATENT DOCUMENTS 1135915  9/1962  Fed. Rep. of Germany ........... 548/309

*Primary Examiner*—Natalie Trousof
*Assistant Examiner*—Natalie Harkaway
*Attorney, Agent, or Firm*—F. X. Murphy; C. J. Knuth; A. J. Nelson

[57] ABSTRACT

Novel spiro-furanohydantoin derivatives useful as aldose reductase inhibitors and as therapeutic agents for the treatment of chronic diabetic complications are disclosed. The compounds include 2-methyl-spiro-[cyclohexa(b)furan-4,4'-imidazolidine]-2',5'-dione, 2-fluoro-spiro-[cyclohexa(b)furan-4,4'-imidazolidine]-2',5'-dione, 2-chloro-spiro-[cyclohexa(b)furan-4,4'-imidazolidine]-2',5'-dione, 2-bromo-spiro-[cyclohexa(b)furan-4,4'-imidazolidine]-2',5'-dione and spiro-[cyclohexa(b)furan-4,4'-imidazolidine]-2',5'-dione.

3 Claims, No Drawings

SPIRO-FURANOHYDANTOIN DERIVATIVES

BACKGROUND OF THE INVENTION

This invention relates to novel spiro-furanohydantoin derivatives useful in the treatment of certain chronic complications arising from diabetes mellitus, such as diabetic cataracts and neuropathy, to pharmaceutical compositions containing such compounds and to a method of using these compounds. Although many oral antidiabetic agents, such as the sulfonyl ureas, effectively lower blood sugar levels, the prevention or alleviation of the chronic complications of diabetes, such as diabetic cataracts, neuropathy, retinopathy and nephropathy has proved harder to achieve. According to U.S. Pat. No. 3,821,383, aldose reductase inhibitors such as 1,3-dioxo-1H-benz[d,e]-isoquinoline-2(3H)-acetic acid and its derivatives are useful in this regard. Spiro-thienohydantoin derivatives are also aldose reductase inhibitors according to U.S. application Ser. No. 870,542. Such compounds inhibit the enzymatic reduction of aldoses, such as glucose and galactose, to the corresponding polyols, such as sorbitol and galactitol, thus preventing or reducing the harmful and unwanted accumulations of polyols in the lens and retina of the diabetically cataractous eye, the diabetically neuropathic peripheral nerve and the diabetically nephropathic kidney.

SUMMARY OF THE INVENTION

The present invention relates to novel aldose reductase inhibitors useful as therapeutic agents for preventing or alleviating chronic diabetic complications. Specifically, the compounds of the present invention are novel spiro-furanohydantoin derivatives of the formula

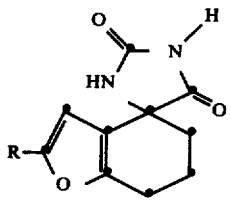

I and the metal salts thereof with pharmaceutically acceptable cations, wherein R is hydrogen, methyl, fluoro, chloro or bromo.

The present invention further comprises a novel method for the treatment of a diabetic host to prevent or alleviate diabetes-associated complications, such as cataracts, neuropathy, nephropathy or retinopathy, which method comprises administering to the host an effective amount of a compound of formula I. Further disclosed is a pharmaceutically-acceptable carrier and a compound of formula I in an amount effective to prevent or alleviate diabetes-associated complications, such as cataracts, neuropathy, nephropathy or retinopathy.

DETAILED DESCRIPTION OF THE INVENTION

The novel compounds of the present invention are readily prepared from an appropriate ketone of the formula

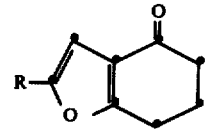

II wherein R is as previously defined. A ketone of formula II is condensed with an alkali metal cyanide, such as sodium cyanide or potassium cyanide, and ammonium carbonate to form the desired spiro-furanohydantoin of formula I. The reaction is normally conducted in the presence of a reaction-inert polar organic solvent in which both the reactants and reagents are mutually miscible. Preferred organic solvents include, but are not limited to, cyclic ethers such as dioxane and tetrahydrofuran, lower alkylene glycols such as ethylene glycol and trimethylene glycol, water-miscible lower alkanols such as methanol, ethanol and isopropanol, and N,N-di(lower alkyl) lower alkanoamides such as N,N-dimethyl formamide, N,N-diethyl formamide and N,N-dimethyl acetamide. In general, the reaction is conducted at a temperature between about 50° C. and about 150° C., perferably about 90° C. to 130° C., for a period of about 2 hours to about 4 days, depending on the temperature employed. Although the amount of reactants and reagents employed in the reaction can vary to some extent, it is preferable to employ at least a slight molar excess of the alkali metal cyanide reagent with respect to the ketone starting material in order to achieve maximum yield. Upon completion of the reaction, the desired product is readily isolated in a conventional manner, for example by first diluting the reaction mixture with water and then cooling the resultant aqueous solution to room temperature, followed by acidification to afford the desired spiro-furanohydantoin compound in the form of a readily-recoverable precipitate.

The starting materials of formula II are readily prepared from the appropriate precursor according to the procedures described in *Bull. Soc. Chim. Fr.*, 1967, 2796.

Pharmaceutically acceptable metal salts can be readily prepared from compounds of formula I by conventional methods. Thus, these salts may be prepared by treating the spiro-furanohydantoins with an aqueous solution of the desired pharmaceutically acceptable metallic hydroxide or other metallic base and evaporating the resulting solution to dryness, preferably under reduced pressure. Alternatively, a lower alkanoic solution of the spiro-furanohydantoin may be mixed with an alkoxide of the desired metal and subsequently evaporating the solution to dryness. The pharmaceutically acceptable metallic hydroxides, bases and alkoxides include those with cations that form metal salts with the acidic compounds of formula I and that are non-toxic at the dosages administered to a subject in need of treatment. Suitable cations for this purpose include, but are not limited to, potassium, sodium, ammonium, calcium and magnesium.

The novel spiro-furanohydantoins of this invention are useful as aldose reductase inhibitors, and as such are of therapeutic value in the treatment of chronic complications of diabetes, such as cataracts, retinopathy, nephropathy and neuropathy. As used in the claims and specification hereof, treatment is meant to include both prevention or alleviation of such conditions. The compounds may be administered to a subject in need of treatment by a variety of conventional routes of administration, including orally and parenterally. In general, these compounds will be administered at dosages between 1 and 250 mg per kg body weight of the subject to be treated per day. However, some variation in dosage will necessarily occur depending on the condition of the subject being treated and the physician will, in any event, determine the appropriate dose for the individual subject.

The compounds may be administered alone or in combination with pharmaceutically acceptable carriers, in either single or multiple doses. Suitable pharmaceutical carriers include inert solid diluents or fillers, sterile aqueous solutions and various nontoxic organic solvents. The pharmaceutical compositions formed by combining the spiro-furanohydantoin and the pharmaceutically acceptable carrier are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tableting purposes. Solid compositions of a similar type may also be employed as fillers in soft and hard-filled gelatin capsules; preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes, and if desired emulsifying or suspending agents, together with diluents such as water, ethanol, propylene glycol, glycerin and combinations thereof.

For parenteral administration, solutions of the spiro-furanohydantoins in sesame or peanut oil or in aqueous propylene glycol may be employed, as well as sterile aqueous solutions of the corresponding water-soluble pharmaceutically acceptable metal salts previously described. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well known to those skilled in the art. Additionally, it is also possible to administer the spiro-furanohydantoin compounds topically, by use of an appropriate opthalmic solution, which may then be administered dropwise to the eye.

The activity of the compounds of the present invention as agents for the control of chronic diabetic complications may be determined by a number of standard biological or pharmacological tests. Suitable tests include (1) measuring their ability to inhibit the enzyme activity of isolated aldose reductase and (2) measuring their ability to reduce or inhibit sorbitol accumulation in the sciatic nerve of acutely streptozotocinized (i.e., diabetic) rats.

The present invention is illustrated by the following examples. It will be understood, however, that the invention is not limited to the specific details of these examples.

EXAMPLE 1

Spiro[cyclohexa(b)furan-4,4'-imidazolidine]-2',5'-dione

A mixture of 2.7 g of cyclohexa(b)furan-4-one (*Bull. Soc. Chim. Fr.*, 1967, 2796), 1.95 g of potassium cyanide and 9.6 g of powdered ammonium carbonate were heated with 40 ml of 95% aqueous ethanol at 110°–120° C. in a steel bomb for 16 hours. The reaction mixture was cooled, diluted with 200 ml of water, and acidified with 12 N hydrochloric acid. The precipitated product was isolated by filtration and recrystallized from ethanol to give 1.73 g of spiro[cyclohexa(b)furan-4,4'-imidazolidine]-2', 5'-dione, mp 245°–248° C.

Analysis: Calcd for $C_{10}H_{10}N_2O_3$: C, 58.24%; H, 4.89%; N, 13.59%. Found: C, 58.31%; H, 4.93%; N, 13.82%.

EXAMPLE 2

2-methyl-spiro[cyclohexa(b)furan-4,4'-imidazolidine]-2',5'-dione

The procedure described in Example 1 was repeated using 2-methyl-cyclohexa(b)furan-4-one (*Bull. Soc. Chim. Fr.*, 1967, 2796) as starting material. 2-methyl-spiro[cyclohexa(b)furan-4,4'-imidazolidine]-2',5'-dione was obtained in 40% yield, mp 234°–236°.

Analysis: Calcd for $C_{11}H_{12}N_2O_3$: C, 59.99%; H, 5.49%; N, 12.72%. Found: C, 59.77%; H, 5.44%; N, 12.80%.

EXAMPLE 3

The spiro-furanohydantoins of Examples 1 and 2 were tested for their ability to reduce or inhibit aldose reductase enzyme activity, following the procedure described in U.S. Pat. No. 3,821,383 and based on the procedure on Hayman et. al., *Journal of Biological Chemistry*, 240, 877 (1965). The substrate employed was partially purified aldose reductase enzyme obtained from calf lens. The results obtained are expressed as the compound concentration that gives 50 percent inhibition of enzyme activity.

| Compound of | 50% Inhibitory Concentration |
| --- | --- |
| Example 1 | $10^{-4}$ M |
| Example 2 | $10^{-4}$ M |

EXAMPLE 4

The compounds of Examples 1 and 2 were tested for their ability to reduce or inhibit sorbitol accumulation in the sciatic nerve of streptozotocinized (i.e., diabetic) rats by the procedure essentially described in U.S. Pat. No. 3,821,383. In the present study, the amount of sorbitol accumulation in the sciatic nerves was measured 27 hours after induction of diabetes. The compounds were administered orally at the dose levels indicated at 4, 8 and 24 hours following the administration of streptozotocin. The results obtained in this manner are presented as the percent inhibition (%) obtained at a 25 mg/kg dose compared to the untreated animal standard (i.e., the untreated animal where sorbitol levels normally rise from approximately 50–100 mM/g. tissue to as high as 400 mM/g. tissue in the 27-hour test period):

| Compound of | Percent Inhibition at 25 mg/kg |
|---|---|
| Example 1 | 46% |
| Example 2 | 2% |

What is claimed is:

1. A spiro-furanohydantoin compound of the formula

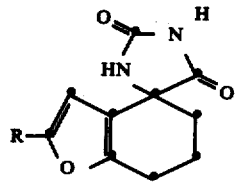

or its pharmaceutically acceptable metal salt, wherein R is hydrogen, methyl, fluoro, chloro or bromo.

2. A pharmaceutical composition of a command of claim 1 which comprises a pharmaceutical formulation of a pharmaceutically-acceptable carrier and a compound of claim 1 in an amount effective to prevent or alleviate diabetes-associated complications.

3. A method for the treatment of a diabetic host to prevent or alleviate diabetes-associated complications which comprises administering to the host an effective amount of a compound of claim 1.

* * * * *